(12) United States Patent
Mayer et al.

(10) Patent No.: US 9,844,402 B2
(45) Date of Patent: *Dec. 19, 2017

(54) ANTERIOR CERVICAL PLATE

(71) Applicant: SpineWelding AG, Schlieren (CH)

(72) Inventors: Jörg Mayer, Niederlenz (CH); Andreas Wenger, Muri b. Bern (CH)

(73) Assignee: SPINEWELDING AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,647

(22) Filed: Dec. 30, 2015

(65) Prior Publication Data

US 2016/0106483 A1    Apr. 21, 2016

Related U.S. Application Data

(62) Division of application No. 13/825,869, filed as application No. PCT/CH2011/000224 on Sep. 22, 2011, now Pat. No. 9,241,740.

(Continued)

(51) Int. Cl.
*A61B 17/88* (2006.01)
*A61B 17/80* (2006.01)
(Continued)

(52) U.S. Cl.
CPC ........ *A61B 17/809* (2013.01); *A61B 17/0642* (2013.01); *A61B 17/7059* (2013.01); *A61B 2017/00004* (2013.01); *A61B 2017/00955* (2013.01); *A61B 2017/0641* (2013.01); *A61F 2002/30449* (2013.01)

(58) Field of Classification Search
CPC ............ A61B 17/8061; A61B 17/7059; A61B 17/8047; A61B 17/8004; A61B 2017/00004; A61B 17/8625; A61B 2017/564; A61B 17/84; A61B 2017/681;
(Continued)

(56) References Cited

U.S. PATENT DOCUMENTS 5,300,074 A    4/1994 Frigg
5,676,666 A    10/1997 Oxland et al.
(Continued)

FOREIGN PATENT DOCUMENTS

JP    2008-543434    12/2006
JP    2008-534141    8/2008
(Continued)

*Primary Examiner* — Eduardo C Robert
*Assistant Examiner* — Tara R Carter
(74) *Attorney, Agent, or Firm* — Rankin, Hill & Clark LLP

(57) ABSTRACT

An anterior cervical includes a plate portion for stabilizing a human or animal spine by being placed ventrally of the spinal column and affixed to two or more different vertebral bodies, and a plurality of fastening portions adapted to be anchored in the different vertebral bodies. At least one of the fastening portions is rigidly connected to the plate portion and includes a sheath element with a longitudinal opening that is accessible from a proximal side and at least one hole that reaches from the longitudinal opening to an outside. The anterior cervical plate further includes a thermoplastic element that may be inserted in the sheath element and that is capable of being liquefied by, for example, mechanical energy acting on the thermoplastic element.

25 Claims, 4 Drawing Sheets

Related U.S. Application Data

(60) Provisional application No. 61/388,243, filed on Sep. 30, 2010, provisional application No. 61/394,580, filed on Oct. 19, 2010.

(51) Int. Cl.
*A61B 17/064* (2006.01)
*A61B 17/70* (2006.01)
*A61B 17/00* (2006.01)
*A61F 2/30* (2006.01)

(58) Field of Classification Search
CPC ............ A61B 17/809; A61B 17/00491; A61B 17/7071; A61B 17/746; A61L 317/809
USPC .................................. 606/280–299, 70, 71
See application file for complete search history.

(56) References Cited

U.S. PATENT DOCUMENTS

| | | | |
|---|---|---|---|
| 6,228,085 | B1 | 5/2001 | Theken et al. |
| 6,558,423 | B1 | 5/2003 | Michelson |
| 6,921,264 | B2 | 7/2005 | Mayer et al. |
| 7,335,205 | B2 | 2/2008 | Aeschlimann et al. |
| 9,241,740 | B2 * | 1/2016 | Mayer ................ A61B 17/0642 |
| 2002/0058939 | A1 | 5/2002 | Wagner et al. |
| 2004/0030341 | A1 | 2/2004 | Aeschlimann et al. |
| 2006/0235405 | A1 | 10/2006 | Hawkes |
| 2006/0287653 | A1 | 12/2006 | Rhyne |
| 2008/0154310 | A1 | 6/2008 | White et al. |
| 2010/0331895 | A1 | 12/2010 | Linke |

FOREIGN PATENT DOCUMENTS

| | | |
|---|---|---|
| JP | 2009-504280 | 2/2009 |
| JP | 2011-525377 | 9/2011 |
| WO | 02/069817 | 9/2002 |
| WO | 2004/017857 | 3/2004 |
| WO | 2008/034277 | 3/2008 |
| WO | 2009/010234 | 1/2009 |
| WO | 2009/010247 | 1/2009 |
| WO | 2009/055952 | 5/2009 |
| WO | 2009/091770 | 7/2009 |
| WO | 2009/132472 | 11/2009 |
| WO | 2010/010522 | 1/2010 |
| WO | 2010/096942 | 9/2010 |
| WO | 2011/054122 | 5/2011 |

* cited by examiner

ANTERIOR CERVICAL PLATE

BACKGROUND OF THE INVENTION

Field of the Invention

The invention is in the field of medical technology. In particular, it relates to an anterior cervical plate and an anterior cervical plate system.

If screws are anchored in live bone tissue, often the problem of insufficient bone stability or insufficient stability of the anchoring in the bone arises. Especially, in trabecular bone tissue, any load acting on the screw is passed over to only few trabeculae, with adverse consequences both for the load bearing capability of the screw-bone connection and for its long-time stability. This is especially severe in osteoporotic or osteopenic or otherwise weakened bone tissue.

Description of Related Art

One solution of this problem is the use of an alternative anchoring method that is suitable also for tissue in which screws are not stable. The publications WO 02/069817, WO 2004/017 857, WO 2008/034 277, and WO 2009/055 952 concern anchorage of an implant in bone tissue with the aid of mechanical vibration and a thermoplastic material which is liquefiable by the mechanical vibration, i.e. the thermoplastic material is capable of being liquefied when vibrated and simultaneously kept in contact with a non-vibrating surface. The thermoplastic material, where in contact with the bone tissue, is liquefied and pressed into pores or cavities of the bone tissue to constitute, when re-solidified, a positive fit connection with the bone tissue.

A special group of embodiments of implants and implant anchoring processes is based on the liquefiable material being inserted (pre-assembled or inserted in situ) in a longitudinal opening of a sheath element. The sheath element comprises at least one hole in the sheath element wall, through which the liquefied material is pressed from the longitudinal opening into the structures (pores or cavities or other structures) of the bone tissue or other hard tissue or hard tissue replacement material in which anchoring is desired. This principle of pressing liquefied material out of a tube or sleeve element with lateral openings is for example described in U.S. Pat. No. 7,335,205, U.S. Pat. No. 6,921, 264, WO 2009/055 952, WO 2009/010247, WO 2009/010234, and PCT application No. PCT/CH 2009/000138, all of which are incorporated herein by reference.

BRIEF SUMMARY OF THE INVENTION

The invention concerns a surgical stabilizer plate. Such a plate comprises a plate portion and a plurality of fastening portions, at least one of one of the fastening portions (and for example all of them) being rigidly connected to the plate portion and comprising a sheath element with a longitudinal opening that is accessible from a proximal side and at least one hole that reaches from the longitudinal opening to an outside. The stabilizer plate further comprises per sheath element a thermoplastic element inserted or insertable in the sheath element and capable of being liquefied by for example mechanical energy acting on the thermoplastic element.

In a group of embodiments, the at least one hole is a radial hole. The radial hole/holes may be arranged at a place different from the distal end of the respective fastening portion, but the fastening portions may distally of the radial hole(s) comprise a stabilizing portion.

An axial extension of the stabilizing portion may be substantial; it may for example be at least two thirds of a distance between the plate portion and the radial holes, or equal or greater than the distance between the plate portion and the radial holes The stabilizing portion may have a non-circular cross section. The distance between the plate portion and the radial hole is for example adjusted so that liquefied material pressed out through the radial hole into surrounding bone tissue after re-solidification provides a sub-cortical anchoring of the ACP.

An example of such a stabilizer plate is an anterior cervical plate (ACP), where the plate portion is capable of stabilizing a human or animal spine by being placed anteriorly (ventrally) of the spinal column and being affixed to two or more different vertebral bodies. The fastening portions in this thus are destined to be anchored in different vertebral bodies.

According to an aspect of the invention, an anterior cervical plate (ACP) is provided, the ACP comprising a plate portion for stabilizing a human or animal spine by being placed ventrally of the spinal column and being affixed to two or more different vertebral bodies, and further comprising a plurality of fastening portions adapted to be anchored in the different vertebral bodies. At least one of one of the fastening portions is rigidly connected to the plate portion and comprises a sheath element with a longitudinal opening that is accessible from a proximal side and at least one hole that reaches from the longitudinal opening to an outside. The anterior cervical plate further comprises per sheath element a thermoplastic element inserted or insertable in the sheath element and capable of being liquefied by for example mechanical energy acting on the thermoplastic element, wherein the hole is positioned so that liquefied thermoplastic material is pressable through the hole into bone tissue of the vertebral body in which the fastener is to be anchored, wherein the at least one fastening portion comprises a stabilizing structure capable of absorbing mechanical loads on the Anterior Cervical Plate.

After the for example mechanical, especially vibration, energy stops impinging on the thermoplastic element, the liquefied material pressed into the bone tissue re-solidifies and thus provides an anchor for the fastening portion and thus for the ACP.

In a group of embodiments, the at least one hole—or at least one of the holes—is a radial hole.

The stabilizing effect of the stabilizer structure is an effect in addition to the anchoring effect of the thermoplastic material. To this end, the fastening portions according to a first option comprise structural features that deviate from a purely rotational cylinder. For example, the fastening portions may have a larger extension in the transverse direction than in the superior/inferior direction. In addition or as an alternative to the first option, the fastening portions according to a second option may comprise a stabilizing portion distally of the hole in that the radial hole/holes are be not arranged at a distal end of the respective fastening portion. The stabilizing portion may have a non-circular cross section and may for example have a larger extension in the lateral (or transverse) direction than in the superior-inferior (cranial-caudal) direction.

The radial holes may be positioned to ensure a sub-cortical anchoring. Generally, a more sub-cortical anchoring may for example be obtained if a distance between an outer surface of the bone tissue and the proximal end of an opening through which the anchoring material exits from the elongate cavity is for example between 2 mm and 7 mm, especially between 3.5 mm and 5.5 mm (this being quantities that hold for grown-up persons). Accordingly, a distance between a distal end face of the plate portion and the proximal onset of the opening can be chosen to be of the same order, i.e. between 2 mm and 7 mm, especially between 3.5 mm and 5.5 mm.

A length (proximodistal extension) of the opening(s) through which the anchoring material exits may be between 1 mm and 6 mm, especially between 2.5 mm and 5 mm. Experiments with sub-cortical anchoring (in vertebral body bone tissue) have shown that for a plurality (for example four) holes equally distributed in the circumferential dimension an anchoring material ring of a proximodistal extension corresponding to the according extension of the openings and of a diameter of 10 mm surrounding a tube element of 4 mm diameter could be obtained.

In embodiments that deal with spine stabilization devices having an intervertebral spacer and in relation to a lateral extension of the vertebral body, sub-cortical anchoring may be achieved if the depth at which the anchoring material exits is between about 5% and 20% of the extension of the vertebral body.

In addition to the fastening portions with a longitudinal opening, the stabilizer plate may comprise conventional fasteners.

In a special embodiment, the stabilizer plate (for example ACP) comprises four fastening portions of the above-described kind being rigidly connected to the plate portion and comprising a longitudinal opening and at least one hole (for example two, three or four radial openings at approximately equal axial positions) from the longitudinal opening to an outside. If the stabilizer plate is an ACP, the fastening portions are then positioned to be driven into the vertebral bodies of two neighbouring vertebrae—two in each.

In an other special embodiment, the stabilizer plate comprises four, five or six fastening portions of the above-described kind being rigidly connected to the plate portion and comprising a longitudinal opening and at least one hole (for example two, three or four radial openings at approximately equal axial positions) from the longitudinal opening to an outside. The ACP in this embodiment reaches over three neighbouring vertebrae, and the fastening portions are then positioned to be driven into the vertebral bodies of at least the uppermost and the lowermost of the three vertebrae, and possible into the vertebral bodies of all of the three vertebrae.

Instruments to implant the stabilizer plate may comprise a template that defines the positions of the indentations to be made in the bone tissue at positions corresponding to the positions of the fastening portions. In accordance with a first option the indentations may be pre-made bores, wherein the template serves for guiding the drill that makes the bores. In accordance with a second option, only the cortical bone is removed or pre-punched (or otherwise prepared) at the locations where the fastening portions are to penetrate into the bone tissue, for example by a drill or other instrument guided by the template. In accordance with an even further option, the fastening portions, then having a sharp tip, may themselves be used for penetrating the cortical bone and advancing into the tissue; the template (if any) may be used to directly guide the stabilizer plate during implantation (by hammering).

The fastening portions, if comprising a plurality of radial holes through which the liquefied thermoplastic material may be pressed, may be configured to comprise a directing structure structured angularly with respect to a longitudinal axis of the longitudinal opening to direct different portions of the liquefiable material to different ones of the radial holes. Such directing structures may be of the kind described in WO 2011/054122.

In embodiments with a plurality of radial holes, these radial holes through which the liquefied material flows out during implantation, may be on a same axial position, or they may be at different axial positions. The angular positions may be evenly distributed around the circumference. In special embodiments, the angular positions may have a deviating distribution adapted for a particular need. For example, if the implant is destined to be an implant for fusing joint parts, and for being inserted in a joint space, the holes (if more than two) may be concentrated on opposed sides to be in contact with the joint areas.

The overall shape of the plate portion can be waisted wherein the waist is formed between the vertebral bodies, and wherein the fasteners are located at the corners. In this, "waisted" means that a transversal extension of the plate portion in a central region (for example between the vertebrae in which the ACP is anchored) is smaller than a transversal extension at the superior/inferior end and is for example smaller than a transversal distance between the axes of the fastening portions. This can imply that the fastening portions are located at the places of the ACP that have the greatest distance from the sagittal plane. This serves the purpose of providing a minimum in lateral plate extension together with a maximum capability of preventing/absorbing lateral bending and torsion.

In a special embodiment, the anterior cervical plate comprises a waisted plate portion with exactly four fastening portions, one fastening portion in each corner. In this, the fastening portions are of the above-described kind and are integral with the plate portion. The anterior cervical plate may in addition comprise an—initially separate—thermoplastic element per fastening portion, the shape of the thermoplastic element adapted for it to be introduced into the longitudinal opening of the respective fastening portion. The plate portion may be bent towards the dorsal side at the corners that carry the fastening portions.

The plate portion need not be plane, nor does it have to have a particular other shape, such as for example a translation symmetry. Rather, it is a particular advantage of the one-piece (integral) construction of the plate portion with the fastening portions that the plate portion can be shaped according to the needs of the user. For example, it can be shaped to take up mechanical loads in a desired manner. Mechanical strengthening can for example have the shape of beads, ridges etc. In addition or as an alternative, the plate portion can be shaped to be adapted to the bone geometry and dimensions and to have a minimal depth away from the vertebral bodies. As a particular example, the anterior cervical plate may be bent to the dorsal direction in proximity to the sagittal plane to minimize irritation to the esophagus or sensible soft tissue structures.

In accordance with a further aspect, the invention thus concerns an anterior cervical plate comprising a plate portion for stabilizing a human or animal spine by being placed ventrally of the spinal column and being affixed to two or more different vertebral bodies, and further comprising a plurality of fastening portions adapted to be anchored in the different vertebral bodies, the fastening portions being rigidly connected to the plate portion and comprising a sheath element with a longitudinal opening that is accessible from a proximal side and at least one hole that reaches from the longitudinal opening to an outside, wherein the hole is positioned so that liquefied thermoplastic material is pressable through the hole into bone tissue of the vertebral body in which the fastener is to be anchored, wherein one or both of the following conditions is fulfilled:

the plate portion is not plane (is uneven)

the fastening portions' outer contour does not have a rotational cylindrical symmetry.

The feature that 'the fastening portions' outer contour does not have a rotational cylindrical symmetry' in this context implies that the shape of the fastening portions is different from rotationally cylindrical in addition to the (for example radial) holes. The fastening portions may have a non-circular outer contour and/or may have at least one trench or the like.

In particular, at least a plurality of the holes may be radial holes, and the fastening portions may comprise a stabilizing portion distally of the radial holes, the stabilizing portion having a larger extension in the transversal direction than in the superior/inferior direction. The plate portion may be waisted in accordance with the above-provided definition. The fastening portions may be carried by the edges of the plate portion, and the edge portions may optionally be bent to the dorsal side. The plate portion may comprise reinforcing ridges or beads.

Also in accordance with the further aspect, the anterior cervical plate may further comprise per sheath element a thermoplastic element inserted or insertable in the sheath element and capable of being liquefied by for example mechanical energy acting on the thermoplastic element.

In other embodiments, the stabilizer plate instead of being an ACP may be a fracture or post-osteotomy stabilizer plate. Osteotomy is a surgical procedure in which a bone is cut with the aim of being shortened, lengthened or re-aligned. Osteotomy is performed on human and animal patients mainly for realigning the load bearing surfaces in joints and for realigning bone portions in particular in the faciomaxillar region but also for re-aligning bone portions healed together with an undesired alignment relative to each other after a fracture. The bone portions separated by the osteotomy procedure mostly need to be re-aligned in a desired position relative to each other and to be stabilized in this position for being able to heal together again. According to the state of the art, osteotomy sites are usually stabilized with the aid of plates (e.g. metal plates) which are positioned on the bone surface across the osteotomy cut and are fastened in this position with the aid of bone screws or nails. Simple bone fractures are stabilized in the same manner.

Especially, the stabilizer plate may be used to stabilize fractures or bone cuts close to human or animal joints, where conventional plates are sometimes not easy to fasten because anchoring of conventional surgical screws is weak. For example, if the plate is to extend from a bone portion at a joint to a bone portion remote from the joint, the anchors of the plate that are closer to the joint may be fastening portions of the above-described kind, whereas for anchoring in bone portions remote from the joint conventional fastening surgical screws may be used. Alternatively, all fastening portions may be of the above-described kind with longitudinal opening and thermoplastic material elements.

Also, generally the stabilizer plate is advantageous in situations where there is little soft tissue to cover the plate (as a consequence, conventional metallic surgical screws tend to cause irritation).

A special application of a stabilizer plate is the stabilization after tibia plateau osteotomy, especially for human, canine or feline patients.

Mechanical vibration or oscillation suitable for devices and methods according to embodiments of the invention that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (sonotrode) is e.g. designed such that its contact face oscillates predominantly in the direction of the element axis (longitudinal vibration) and with an amplitude of between 1 and 100 μm, preferably around 10 to 30 μm. Rotational or radial oscillation is possible also.

For specific embodiments of devices, it is possible also to use, instead of mechanical vibration, a rotational movement for creating the named friction heat needed for the liquefaction of the anchoring material. Such rotational movement has preferably a speed in the range of 10'000 to 100'000 rpm. A further way for producing the thermal energy for the desired liquefaction comprises coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infrared frequency range is used, wherein the preferred radiation source is a corresponding laser. Electric heating of one of the device parts may also be possible.

In this text the expression "thermoplastic material being liquefiable e.g. by mechanical vibration" or in short "liquefiable thermoplastic material" or "liquefiable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 μm and 100 μm, preferably around 10 to 30 μm. Such vibrations are e.g. produced by ultrasonic devices as e.g. known for dental applications. For being able to constitute a load-bearing connection to the tissue, the material has an elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www.matweb.com by Automation Creations, Inc.). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 μm (contents, preferentially 10-25% by volume), submicron (nanofillers as from precipitation, preferentially plate like aspect ratio>10, 10-50 nm, contents 0.5 to 5% by volume).

A specific example of a material with which experiments were performed was PLDLA 70/30 comprising 30% (weight percent) biphase Ca phosphate that showed a particularly advantageous liquefaction behaviour.

The material of the ACP may be any material that does not melt at the melting temperatures of the liquefiable material. Especially, the sheath element may be of a metal, for example a titanium alloy. A preferred material is titanium grade 5. This material, in addition to being generally suited for implantable devices, has a comparably low heat conduction. Because of this bad heat conduction, the melting zone arising in liquefiable material is heated quickly, without the surroundings being heated to too high temperatures. Alternative materials for the ACP are other metals like other titanium alloys, stainless steel, or hard plastics such as PEEK etc.

BRIEF DESCRIPTION OF THE DRAWINGS

In the following, ways to carry out the invention and embodiments are described referring to drawings. The drawings mostly are schematical. In the drawings, same reference numerals refer to same or analogous elements. The drawings show.

DESCRIPTION OF THE PREFERRED EMBODIMENTS

Figure 1:
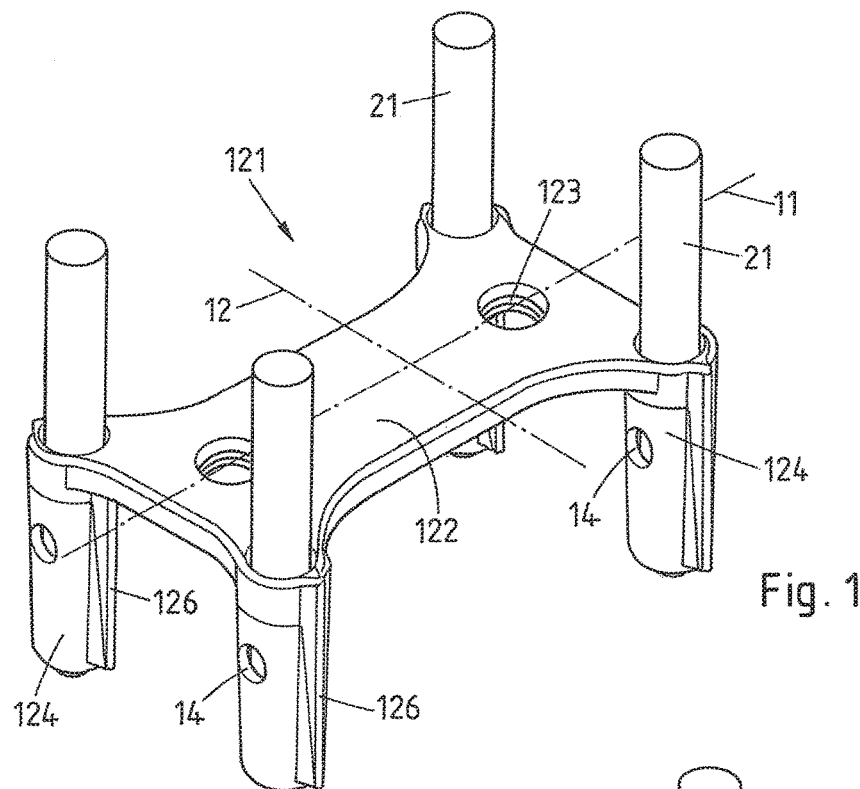
FIG. 1 is a perspective view of an embodiment of an anterior cervical plate (ACP)
Figure 2:
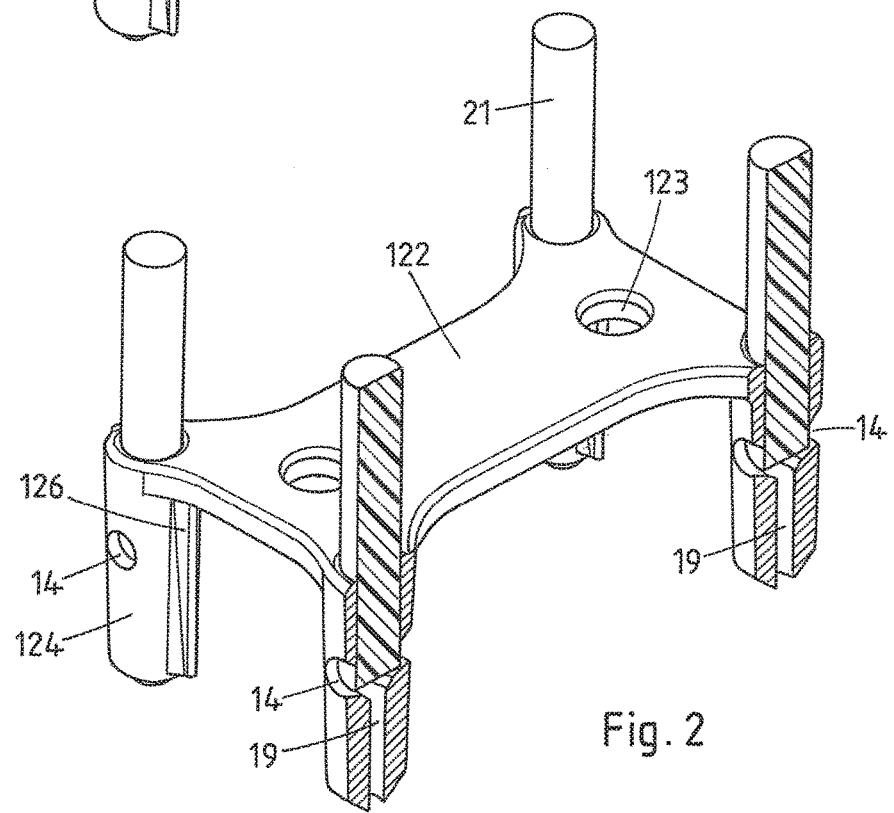
FIG. 2 is a partial sectional perspective view of FIG. 1.

In FIGS. 1 and 2, an anterior cervical plate (ACP) 121 is depicted. The ACP has a plate portion 122 for stabilizing a human (or animal) spine by being placed anteriorly (ventrally) of the spinal column and being affixed to two (or more) different vertebral bodies. The plate portion may have a shape of a kind known in the art that may be adapted to the particular needs of the patient. For example, in contrast to the depicted embodiment, the plate portion may comprise holes shaped according to biomechanical considerations to provide some elasticity for certain movements while providing a desired stiffness against other movements.

In the embodiment of FIG. 1, the plate portion has two holes 123 with an inner thread that may serve for holding the plate during surgical operation, while the variant of FIG. 2 has two holes 123 without any thread. Apart from this difference, the embodiments of FIGS. 1 and 2 may be identical.

The ACP may be used for stabilizing a section of the human spine with or without an interbody fusion implant between two vertebral bodies. Especially, the ACP may be used in connection with an interbody fusion implant as disclosed in WO 2010/096942 incorporated herein by reference.

The thermoplastic elements 21 may be initially separate from the fastening portions. In the depicted embodiment, they have the shape of a rotational cylinder, but other shapes—adapted to the shape of the longitudinal opening—are possible.

In FIG. 1, also the longitudinal axis 11 (that, after operation, is destined to be parallel to the longitudinal (cranial-caudal; superior-inferior) axis of the vertebra and thus to the sagittal plane) and the transversal axis 12 (that after implantation is to be parallel to the lateral (left-right/mediolateral) axis of the patient's body) of the ACP are depicted. In the present text, generally the directions "longitudinal", "transversal/lateral", "dorsal" and "ventral" refer to the axes and directions when the ACP is placed in the body in the intended manner.

In addition to the plate portion 122, the ACP has a plurality of (four in the depicted embodiment) fastening portions 124. Each fastening portion is rigidly connected to the plate portion 122 and for example one-piece (integral) with it. Each fastening portion has the shape of a sheath element (tube element) with a longitudinal opening that is accessible from the proximal side and at least one radial hole 14 (two holes in the depicted configuration) through which, after liquefaction, especially by mechanical energy, the thermoplastic material can be pressed out for anchoring.

The radial holes 14 are arranged at a distance to the plate that ensures sub-cortical anchoring.

The depicted embodiment comprises, in addition to the radial holes 14, a distal, axial hole 19 per tube element. The purpose of the distal, axial hole 19 is the same as the corresponding distal, axial hole of the above-described embodiments. In alternative embodiments—described in somewhat more detail below—only a distal hole is present in at least one fastening portion 124 instead of a radial hole.

In the shown embodiment, the fastening portions 124 comprise, distally of the radial openings 14, a substantial extension serving as additional stabilizers. Especially, the main load acting on an ACP is initiated by flexures along the longitudinal axis of the spinal column, which will cause forces in the up-down direction (in the orientation of the figure) on the distal ends of the fastening portions. The longer distal extension helps to absorb such loads.

In addition or as an alternative, the fastening portions may comprise wings 126 that extend in lateral directions. Such wings or other deviations from a circular shape may be advantageous—especially if they make the transverse extension (extension in a direction perpendicular to the direction that connects neighboring vertebra) larger than the superior-inferior extension (extension in the direction along the local axis of the spinal column/cranial-caudal axis)—so that again the loads that arise from flexions of the spinal column may be ideally absorbed.

Also for other applications than the application as an ACP, such non-circular cross sections of the additional stabilizers may be advantageous—depending on restrictions on the extensions of the fastening portions and the loads to be borne by the stabilizer plate.

Further, as an alternative to the depicted configuration, it may be advantageous to make the fastening portions less stiff and more flexible than the often very stiff tube shape, for example by making it blade-shaped. A too high stiffness can be problematic in situations where it is not desired to fully transmit every momentum acting on the fastener onto the bone trabeculae but to absorb some by a some elasticity of the fastener. A blade shape may by more flexible than a tube shape. Also, a blade shape, for which no opening in the bone tissue has to be pre-made during surgical insertion, is less of an exposure of the bone tissue than a tube shape reaching further distally would be.

The fastening portions or at least one of the fastening portions may be shaped in accordance with the first aspect of the invention, i.e. the tube elements or at least one of the tube elements may comprise a directing structure that is structured angularly with respect to a longitudinal axis of the longitudinal opening to direct different portions of liquefiable material from a liquefiable element to different ones of the holes 14.

While in the depicted embodiment, the ACP comprises four fastening portions, each with a longitudinal opening for a liquefiable element to be inserted, this is not necessary. For example the ACP may comprise a combination of fastening portions of the described kind with conventional fasteners such as surgical screws that have to be inserted through fastening holes. For example the ACP may comprise conventional fasteners for anchoring in stronger, healthier bone tissue and fastening portions for sub-cortical anchoring of the described kind at locations where the bone tissue is weaker and/or less dense.

In other variants, it is possible to replace at least some of the fastening portions that are rigidly attached to the plate portion by tube elements that can be separately introduced, for example in the manner described in WO 2010/096942 incorporated herein by reference.

Also, the total number of fastening portions does not need to be four but may be an other suitable number, for example three, five or six. It is further possible that the ACP extends not only across two vertebrae but across more vertebrae, for example three vertebrae, whereas the ACP may be anchored in all vertebrae across which it extends (for example by two fastening portions for each) or, in special situations (for example with a partially removed vertebra) only in some of them, for example the topmost and lowest vertebrae of a series of three vertebrae.

In all embodiments, the plate portion and the fastening portions may be made of a metal, for example titanium or stainless steel. In alternative embodiments, they may also be made of a non-resorbable plastic, such as PEEK. It is also possible to make them of a resorbable plastic, such as a PLA. If the plate portion and the fastening portions are made of a thermoplastic, the softening temperature should preferably be higher than the softening temperature of the thermoplastic elements insertable in the sheath elements of the fastening portions, so that only the thermoplastic elements and not the fastening portions liquefy. Often, a softening temperature difference of 20° C. (or more) is sufficient for assuring this.

For implanting, the surgeon may optionally in a first step locally remove the cortical bone tissue at the locations where the fastening portions are to be driven into the vertebral bodies. Thereafter, the ACP is inserted; if necessary it may be hammered to drive the fastening portions fully into the bone tissue until the plate portion abuts against the cortical bone. Then, if the fastening portions do not already comprise a thermoplastic element, such a thermoplastic element is introduced into the longitudinal opening from the proximal side thereof. An insertion tool with a mechanical vibration generator (such as an ultrasonic transducer) and a sonotrode is used to at least partly liquefy thermoplastic material of the thermoplastic element at the distal end thereof to drive this material through the holes 14 into the surrounding tissue. The sonotrode, for this purpose, may have a cross sectional area slightly smaller than the cross sectional area of the longitudinal opening so that it drives the thermoplastic element deeper into the opening.

Figure 3:
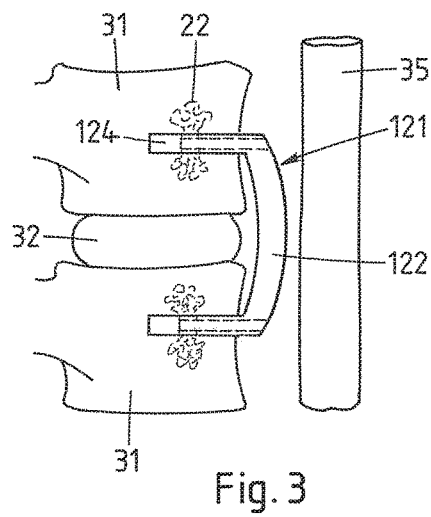
FIG. 3 is an elevation view illustrating the use of an embodiment of a anterior cervical plate.
Figure 4:
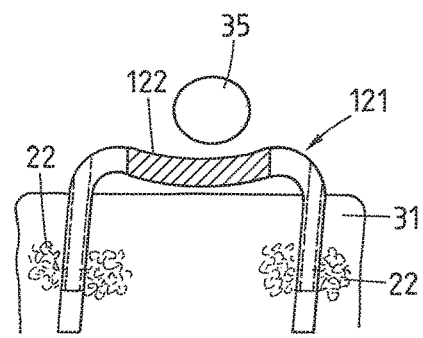
FIG. 4 is a partial sectional plan view of an anterior cervical plate with an esophagus.

Whereas in the hereinbefore described embodiment, the plate portion is depicted to be essentially plane and the fastening portions are essentially perpendicular to the plate portion, this need not be the case. A main advantage of the approach according to the invention that comprises fastening portions to be integrally formed with the plate portion is that mechanically stable constructions are possible that when implanted extend only minimally away from the vertebral bodies. Such constructions may comprise non-plane plate portions. A very schematically depicted first approach is shown in FIG. 3. The anterior cervical plate is implanted by being anchored in two neighboring vertebral bodies 31. An intervertebral disk is shown between the intervertebral bodies; as the case may be instead of a natural intervertebral disk, an interbody spacer (cage) may be placed to replace the intervertebral disk previously to anchoring the ACP. Thermoplastic material portions 22 that during the anchoring process exited through the holes 14 into the surrounding tissue is schematically shown in FIG. 3. As may be the case for any embodiment, the fastening portions are positioned to be anchored centrally with respect to the superior-inferior axis in the vertebral bodies. Whereas anterior cervical plates according to embodiments of the invention can be designed for stabilizing different kinds of vertebrae, namely lumbar vertebrae, thoracic vertebrae and cervical vertebrae, the embodiment of FIG. 3 pertains to vertebrae of the upper thorax. In FIG. 3, the esophagus 35 is also shown schematically. If an anterior cervical plate is implanted, its configuration and location should make sure that the esophagus is not irritated despite being rather close to the vertebral column. FIG. 4 illustrates, in schematic section through a transversal plane, a possible configuration with the plate being bent, in a central region (around the longitudinal axis of the ACP/in proximity to the sagittal plane), towards the dorsal direction to provide more space for the esophagus 35.

Figure 5A:
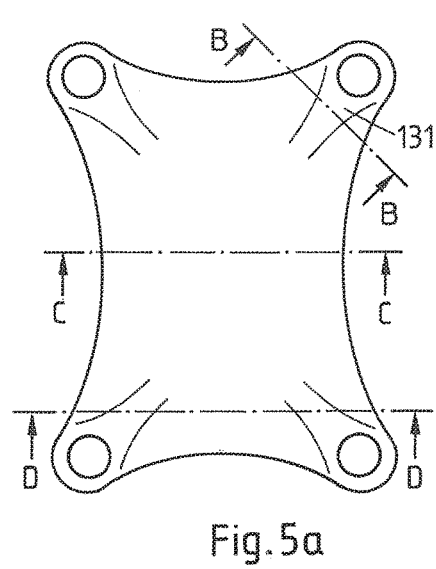
FIG. 5a is a plan view of an embodiment of an anterior cervical plate with reinforcing beads.
Figure 5B:
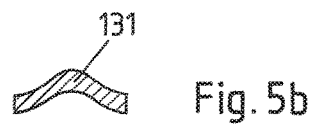
FIG. 5b is a sectional elevation view of FIG. 5a taken along line B-B.
Figure 5C:
FIG. 5c is a sectional elevation view of FIG. 5a taken along line C-C.
Figure 5D:
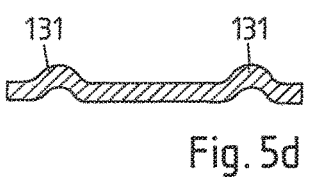
FIG. 5d is a sectional elevation view of FIG. 5a taken along line D-D.

The plate portion can be comparably thin and nevertheless have sufficient mechanical stability. FIGS. 5*a*-5*d* show a configuration in which beads 131 that range from the corner regions, in continuity with which the fastening portions are made, towards the center and decrease towards the center are shown. FIGS. 5*b*, 5*c*, and 5*d* show sections along the lines B-B, C-C and D-D in FIG. 5*a*, respectively. The features illustrated in FIG. 3 (a concave configuration bent towards the ventral side in a longitudinal section (section along the sagittal plane); a central region being bent towards the dorsal side in transversal section; the beads; and/or the sloping corner portions) can be arbitrarily combined, i.e. all these features can be combined with each other, or sub-groups of two, or three of these features can be combined in any grouping; further, the anterior cervical plate need not be symmetrical but can also be asymmetrical (for example the beads/and or the sloping corners can be present on one side only etc.).

The shape of the plate portion illustrated with respect to FIGS. 5*a*-5*d* is merely an example. The way the plate portion differs from a plane configuration may be altered in many ways. For example, it would be possible to provide the plate portion with ridges instead of the illustrated beads. Also, the beads could be bent to project into the opposed direction and/or could be placed elsewhere. Depending on the anatomy around the ACP, overall plate 3D structure can be chosen in many different ways.

Figure 6:
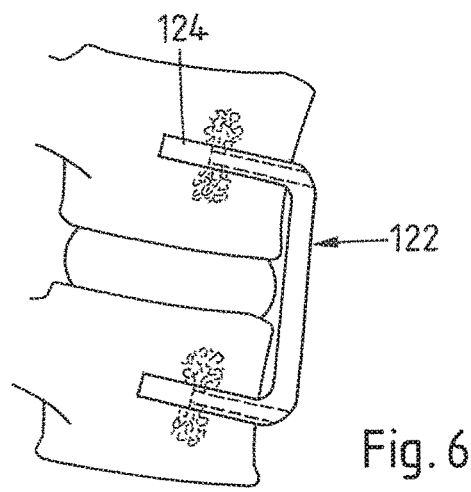
FIG. 6 is an elevation view of an asymmetric anterior cervical plate in use.

FIG. 6 schematically illustrates a configuration where the fastening portions 124 are not at right angles to the plate portion but at a different angle. Generally, the fastening portions (or at least those fastening portions that are integral with the plate portion) are approximately parallel to each other.

Figure 7A:
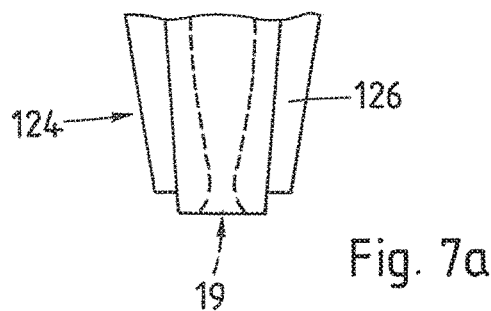
FIG. 7a is an elevation view of the distal end of an alternative fastening portion.
Figure 7B:
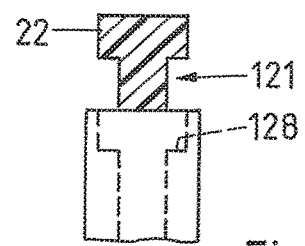
FIG. 7b is an elevation view of the proximal end of an alternative fastening portion.

FIGS. 7*a* and 7*b* show a variant of a fastening portion 124. In this variant, the fastening portion does not comprise any radial hole but only a distal hole 19 through which the liquefied material exits into the surrounding tissue. In order to give the configuration stability against movements of the ACP in ventral directions, the longitudinal opening comprises a shoulder 128 that cooperates with a proximal broadening 22 of the thermoplastic element 21.

Figure 8:
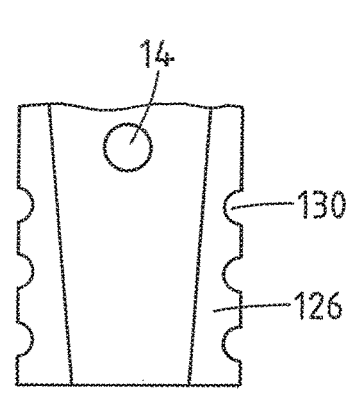
FIG. 8 is an elevation view of a distal end region of a further variant of a fastening portion.
Figure 9:
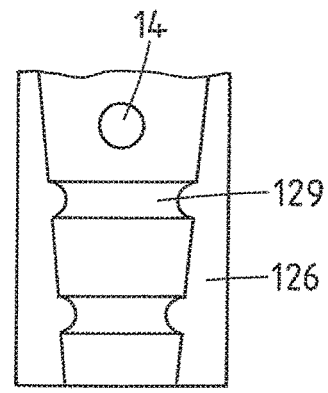
FIG. 9 is an elevation view of a distal end region of a further variant of a fastening portion.

FIGS. 8 and 9 yet illustrate the possibility to provide the fastener with a non-reaming retention structure into which the bone tissue may grow to ensure a long-term stability of the anchoring.

FIG. 8 shows a distal region of a fastening portion, with wings 126, similar to the embodiment of FIGS. 1 and 2. The wings are provided with indentations 130 (in alternative configurations, the outer contour could comprise a wave shape). These indentations form a non-reaming retention structure that does not cause a substantial additional resistance against insertion of the fastening portion of the anterior cervical plate. In the time after implantation, bone tissue can grow into the retention structures so that the anchoring in the bone tissue gains additional stability. The approach of providing the fastening portions with an outer retention structure can be combined with the use of a resorbable thermoplastic material.

Another example of non-reaming retention structures is illustrated in FIG. 9. The fastening portion comprises circumferential ridges 129 serving as retention structures. Combinations of retention structures of the wings 126 (if present, as illustrated in FIG. 8) and of the fastening portion body (as shown in FIG. 9) are possible. In addition or as an alternative, micro-retention structures can be used, such as an intended surface roughness of the fastening portion or a part of it. A maximum surface roughness of such portions can for example be between 1 µm and 100 µm, especially between 1 µm and 50 µm or 20 µm, for example between 2 µm and 10 µm.

Figure 10:
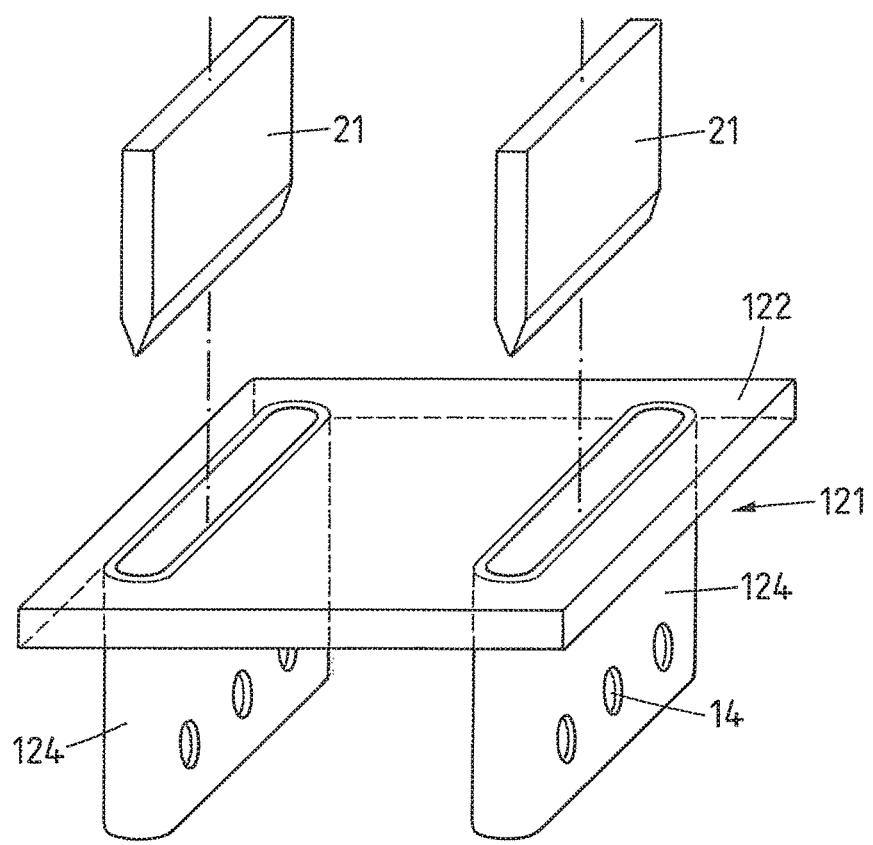
FIG. 10 is a partially exploded perspective view of an alternative embodiment of an anterior cervical plate.

The stabilizing structure in most of the hereinbefore described embodiments comprises a stabilizing portion distally of the radial holes through which the liquefied thermoplastic material exits. Alternative configurations are possible, for example fastening portions that have an elliptical or otherwise elongate cross section, especially to have a larger extension in the transversal direction than in the superior/inferior direction. An example where this is taken to an extreme is depicted in FIG. 10. The embodiment of FIG. 10 comprises only two fastening portions 24 that have a substantial transversal extension. In contrast to the hereinbefore described embodiments, the thermoplastic elements 21 are not pin-shaped but have a shape adapted to the shape of the fasting portions 124. In the depicted embodiment, the radial holes 14 are arranged at the distal end of the fastening portions. However, the configuration of FIG. 10 could also be implemented with more proximal radial holes, for example for sub-cortical anchoring.

What is claimed is:

1. A surgical stabilizer plate, comprising a plate portion for stabilizing a human or animal spine by being affixed to at least one vertebral body, the plate portion comprising a proximal side and a distal side, the distal side being adapted to lie against the at least one vertebral body, the plate portion comprising a plurality of plate openings accessible from the proximal side, and comprising, for each plate opening, a fastening portion, said fastening portion:
being integral with the plate portion;
extending from the plate opening to the distal side, at an angle to the plate opening;
being adapted to be anchored in one of the at least one vertebral body;
comprising a sheath portion with a longitudinal opening that is accessible from the proximal side and opens into the plate opening, whereby the plate opening forms a mouth of the longitudinal opening;
and with at least one hole that reaches from the longitudinal opening to an outside;
wherein the stabilizer plate further comprising, per fastening portion, a thermoplastic element inserted or insertable in the longitudinal opening and capable of being liquefied by energy acting on the thermoplastic element, wherein the hole is positioned so that liquefied thermoplastic material is pressable through the hole into bone tissue of the vertebral body in which the fastening portion is to be anchored.

2. The stabilizer plate according to claim 1, wherein at least one fastening portion comprises a stabilizing structure capable of absorbing mechanical loads on the stabilizer plate.

3. The stabilizer plate according to claim 1, wherein the at least one hole is a radial hole.

4. The stabilizer plate according to claim 3, wherein at least one fastening portion comprises a plurality of radial holes that are at different axial positions.

5. The stabilizer plate according to claim 3, wherein at least one fastening portion comprises a plurality of radial holes having angular positions that deviate from being evenly distributed around a circumference of the fastening portion.

6. The stabilizer plate according to claim 3, wherein the stabilizing structure comprises a stabilizing portion distally of the radial hole.

7. The stabilizer plate according to claim 6, wherein a distance between the plate portion and the at least one radial hole is adjusted so that liquefied material pressed out through the radial hole into surrounding bone tissue after re-solidification provides a sub-cortical anchoring.

8. The stabilizer plate according to claim 7, wherein an axial extension of the stabilizing portion is at least two thirds of a distance between the plate portion and the radial hole.

9. The stabilizer plate according to claim 6, wherein an axial extension of the stabilizing portion is at least two thirds of a distance between the plate portion and the radial hole.

10. The stabilizer plate according to claim 1, wherein the fastening portions have a non-circular cross section.

11. The stabilizer plate according to claim 10, wherein a transversal extension of the fastening portions is greater than an extension in a superior-inferior direction.

12. The stabilizer plate according to claim 11, wherein at least one of the fastening portion comprises a wing projection from a fastening portion body.

13. The stabilizer plate according to claim 10, wherein at least one of the fastening portion comprises a wing projection from a fastening portion body.

14. The stabilizer plate according to claim 1, wherein the plate portion has a waisted shape.

15. The stabilizer plate according to claim 1, wherein the plate portion comprises at least one of ridges and beads.

16. The stabilizer plate according to claim 15, wherein the beads range from the corner regions of the plate portion toward the center.

17. The stabilizer plate according to claim 16, wherein the beads decrease toward the center.

18. The stabilizer plate according to claim 1, wherein the plate portion is bent.

19. The stabilizer plate according to claim 1, wherein at least one of the fastening portions comprises an indentation serving as a non-reaming retention structure.

20. The stabilizer plate according to claim 19, wherein the at least one fastening portion with the indentation further comprises a wing extending in a lateral direction, and the indentation is an indentation in the wing.

21. The stabilizer plate according to claim 19, wherein the indentation is a circumferential ridge.

22. The stabilizer plate according to claim 1, wherein the fastening portion comprises a surface roughness serving as a retention structure.

23. The stabilizer plate according to claim 22, wherein a maximum surface roughness of the retention structure is between 1 μm and 100 μm.

24. The stabilizer plate according to claim 1, wherein the plate portion is non-planar.

25. The stabilizer plate according to claim 1, wherein the plate portion is affixed to two or more different vertebral bodies by at least one of the fastening portions extending into a first one of the vertebral bodies and at least another one of the fastening portions extending into a second one of the vertebral bodies.

* * * * *